United States Patent
Jullien et al.

(10) Patent No.: US 10,267,732 B2
(45) Date of Patent: Apr. 23, 2019

(54) METHOD FOR DETECTION OF A REVERSIBLY PHOTO-CONVERTIBLE FLUORESCENT SPECIES

(71) Applicants: CENTRE NATIONAL DE LA RECHERCHE SCIENTIFIQUE, Paris (FR); INSTITUT CURIE, Paris (FR); ECOLE NORMALE SUPERIEURE DE PARIS, Paris (FR); UNIVERSITE PIERRE ET MARIE CURIE, Paris (FR)

(72) Inventors: Ludovic Jullien, Arcueil (FR); Thomas Le Saux, Paris (FR); Arnaud Gautier, Paris (FR); Vincent Croquette, Antony (FR); Nath Sarang, New Delhi (IN); Pencheng Wang, Saint Louis, MO (US); Jérôme Querard, Montrouge (FR); Samantha Albright, Boston, MA (US)

(73) Assignees: CENTRE NATIONAL DE LA RECHERCHE SCIENTIFIQUE, Paris (FR); INSTITUT CURIE, Paris (FR); ECOLE NORMALE SUPERIEURE DE PARIS, Paris (FR); UNIVERSITE PIERRE ET MARIE CURIE, Paris (FR)

( * ) Notice: Subject to any disclaimer, the term of this patent is extended or adjusted under 35 U.S.C. 154(b) by 82 days.

(21) Appl. No.: 15/034,402

(22) PCT Filed: Nov. 21, 2014

(86) PCT No.: PCT/EP2014/075336
§ 371 (c)(1),
(2) Date: May 4, 2016

(87) PCT Pub. No.: WO2015/075209
PCT Pub. Date: May 28, 2015

(65) Prior Publication Data
US 2016/0356716 A1 Dec. 8, 2016

(30) Foreign Application Priority Data

Nov. 21, 2013 (FR) ...................... 13 61476

(51) Int. Cl.
*A61K 49/00* (2006.01)
*G01N 21/64* (2006.01)
*G01N 33/53* (2006.01)

(52) U.S. Cl.
CPC ..... *G01N 21/6408* (2013.01); *A61K 49/0017* (2013.01); *G01N 21/6428* (2013.01); *G01N 21/6458* (2013.01); *G01N 33/5306* (2013.01); *G01N 2201/12* (2013.01)

(58) Field of Classification Search
CPC ........... A61K 49/0017; C12N 2529/10; G01N 2500/10; G01N 21/6458; G01N 21/6428; G01N 21/6408; G01N 2201/12; G01N 2021/6439; G01J 3/0218; G01J 3/44; G02B 21/06; G02B 21/16; G02B 26/06; G02B 27/58
See application file for complete search history.

(56) References Cited

FOREIGN PATENT DOCUMENTS

| GB | 2 089 029 A | 6/1982 |
|---|---|---|
| WO | 01/27883 A1 | 4/2001 |

OTHER PUBLICATIONS

P. Wang et al., "Photochemical properties of Spinach and its use in selective imaging," Chemical Science, vol. 4, No. 7, Jan. 1, 2013, pp. 2865, XP055131010.

*Primary Examiner* — Mary K Zeman
(74) *Attorney, Agent, or Firm* — Baker & Hostetler LLP

(57) ABSTRACT

A method for detection of at least one reversibly photo-convertible fluorescent species, comprises the following steps: a) illumination of a sample comprising said or at least one of the reversibly photo-convertible fluorescent species by a periodically modulated illuminating light; and b) detection of fluorescent emission emitted by the sample thus illuminated; wherein the method further comprises the following step: c) extraction of the amplitude of the intensity component of the fluorescent emission exhibiting the same periodicity as the periodically modulated illuminating light and a phase quadrature with respect to the same; and wherein the mean intensity of the illuminating light and the modulation frequency of the same are chosen to maximize the amplitude of the intensity component of the fluorescent emission.

17 Claims, 10 Drawing Sheets

US 10,267,732 B2

METHOD FOR DETECTION OF A REVERSIBLY PHOTO-CONVERTIBLE FLUORESCENT SPECIES

CROSS-REFERENCE TO RELATED APPLICATIONS

This application is a National Stage of International patent application PCT/EP2014/075336, filed on Nov. 21, 2014, which claims priority to foreign French patent application No. FR 1361476, filed on Nov. 21, 2013, the disclosures of which are incorporated by reference in their entirety.

FIELD OF THE INVENTION

The invention relates to a method for detecting a reversibly photoswitchable fluorescent species. Such a method offers numerous applications, notably in chemistry, in biology and in the field of environmental measurements.

BACKGROUND

A "species" should be understood to be a chemical species such as a molecule or a complex, or a physical object such as a nanoparticle. "Reversibly photoswitchable species" should be understood to mean a species exhibiting at least two distinct states, having different fluorescence properties, and being able to switch from one state to the other reversibly by the effect of light. Examples of reversibly photoswitchable fluorescent species are the protein "Dronpa" and the complex "Spinach—DFHBI" ("Spinach" being an aptamer of RNA and DFHBI being a fluorogenic probe). These species can, in particular, be used as probes or markers.

Imaging, and more particularly fluorescence microscopy, has become an essential tool in biology, but also in other disciplines such as materials science. Its applications, however, are limited by the capacity to observe a signal of interest in a background of fluorescence or of noise. This problem is particularly acute in in vivo imaging applications, in which the fluorescent markers to be detected are scattered in a complex self-fluorescent and/or light-scattering medium; the useful signal is then embedded in an intense background noise.

Another limitation of the conventional fluorescence detection and imaging techniques lies in the fact that numerous fluorophores exhibit wide emission bands; consequently, it is difficult to selectively detect a number of fluorescent markers in one and the same sample, because their emission spectra tend to be superimposed.

To overcome these limitations, it has been proposed to use reversibly photoswitchable fluorescent probes, an illumination that is modulated (variable in time in a predetermined manner) and a demodulation of the detected fluorescence signal. That makes it possible to exploit the temporal dynamics of a reversibly photoswitchable probe—which is specific to it and is different from that of interfering fluorophores—to extract a useful signal from the background noise; this is then called "dynamic contrast".

One technique known from the prior art exploiting this principle is known by the name of OLID, an acronym for "Optical Lock-In Detection". It is described in the article by G. Marriott et al. "Optical lock-in detection imaging microscopy for contrast-enhanced imaging in living cells", PNAS, vol. 105, no. 46, pages 17789-17794 (18 Nov. 2008). One drawback with this technique is that it does not provide quantitative information on the concentration of the reversibly photoswitchable fluorophore. Also, it requires a light excitation sequence with two colors and at least one reference pixel.

Another technique known from the prior art using a photoswitchable fluorescent probe and a modulated excitation is known by the name of SAFIRe, an acronym for "Synchronously Amplified Fluorescence Image Recovery". It is described in the article by Ch. I. Richards et al. "Synchronously Amplified Fluorescence Image Recovery (SAFIRe)", J. Phys. Chem. B 2010, 114, 660-665. This technique also uses a two-color excitation. The optimization of the dynamic contrast has the drawback of being done empirically, which introduces an additional implementation complexity.

The article by Q. Wei and A. Wei "Optical Imaging with Dynamic Contrast Agents", Chem. Eur. J., 17, 1080-1091 reports on a number of known dynamic contrast techniques. In addition to the abovementioned OLID and SAFIRe techniques, based on an optical modulation of the fluorescence, this article describes techniques that exploit a magnetomotive or photothermal modulation. These techniques are complex to implement, precisely because they require both an optical system for the excitation and the detection of the fluorescence and a non-optical (magnetic or thermal) modulation system.

Thus, all the fluorescence detection techniques known from the prior art exploiting a dynamic contrast have the drawback of a relatively complex implementation. Furthermore, none of them offers sufficient selectivity to allow for the successive detection of a significant number (of the order of 10, even more) of fluorescent species in one and the same sample. Moreover, these techniques have been developed exclusively for microscopic applications and cannot be easily transposed to the remote sensing of fluorescent species in the environment.

SUMMARY OF THE INVENTION

The invention aims to overcome at least one of the abovementioned drawbacks of the prior art.

One subject of the invention that makes it possible to achieve this aim is a method for detecting at least one reversibly photoswitchable fluorescent species, comprising the following steps:

a) illuminating a sample containing said or at least one said reversibly photoswitchable fluorescent species with a periodically modulated illuminating light; and b) detecting a fluorescence emission emitted by said duly illuminated sample; characterized in that it also comprises the following step:

c) extracting the amplitude of the component of the intensity of said fluorescence emission exhibiting the same periodicity as said periodically modulated illuminating light and in phase quadrature in relation thereto;

and in that the average intensity of said illuminating light and its modulation frequency are chosen so as to maximize said amplitude of the intensity component of said fluorescence emission.

According to different embodiments of the invention:

at least one said reversibly photoswitchable fluorescent species (P) exhibits a first chemical state and a second chemical state, at least one of said states being fluorescent, said or each said reversibly photoswitchable fluorescent species (P) being able to be switched from said first state to said second state by a first photo-induced reaction, then return to said first state both by a thermo-induced reaction and by a second photo-induced reaction and said illuminating light can exhibit an average intensity $I^0$ and be modulated at a frequency f with:

$$I^0 = \frac{k_{21}^\Delta}{\sigma_{12} + \sigma_{21}}$$

$$f = k_{21}^\Delta / \pi$$

in which:

$\sigma_{12}I^0$ and $\sigma_{21}I^0$ are, respectively, the kinetic constants of said first photo-induced reaction of said fluorescent species and of said second photo-induced reaction of said fluorescent species; and $k\Delta_{21}^\Delta$ is the kinetic constant of said thermo-induced reaction of said fluorescent species.

In said step a), said sample can be illuminated by a substantially monochromatic illuminating light.

Said illuminating light (FEX) comprises a first substantially monochromatic illuminating light (FEX1) of wavelength $\lambda_1$ and a second substantially monochromatic illuminating light (FEX2), of wavelength $\lambda_2$, different from $\lambda_1$, the first and the second said illuminating lights being adapted to induce the photoswitching of said states of at least one said reversibly photoswitchable fluorescent species (P) and of which at least the first said illuminating light is periodically modulated.

At least one said reversibly photoswitchable fluorescent species (P) exhibits a first chemical state and a second chemical state, at least one of said states being fluorescent, said or each said reversibly photoswitchable fluorescent species (P) being able to be switched from said first state to said second state by a first photo-induced reaction, then return to said first state by a second photo-induced reaction, and in which said first illuminating light exhibits an average intensity $I_1^0$ and is modulated at a frequency f' and said second illuminating light exhibits a substantially constant intensity $I_2^0$ with:

$$\frac{I_2^0}{I_1^0} = \frac{\sigma_{12,1} + \sigma_{21,1}}{\sigma_{12,2} + \sigma_{12,2}}$$

$$\frac{f'}{I_1^0} = (\sigma_{12,1} + \sigma_{21,1})/\pi$$

in which:

$\sigma_{12,1}I_1^0$ and $\sigma_{21,1}I_1^0$ are, respectively, the kinetic constants of said first and said second reactions photo-induced by said first illuminating light; and $\sigma_{12,2}I_2^0$ and $\sigma_{21,2}I_2^0$ are, respectively, the kinetic constants of said first and said second reactions photo-induced by said second illuminating light.

Said sample can contain a plurality of said reversibly photoswitchable fluorescent species exhibiting different dynamic properties, said steps a) to c) being implemented successively for the detection of at least two said reversibly photoswitchable fluorescent species.

Said steps b) and c) can be implemented by lock-in detection of said fluorescence emission.

Said sample can contain at least one other fluorescent species.

The method can also comprise the following step:

d) determining the concentration of said or of at least one said reversibly photoswitchable fluorescent species from the component of the intensity of said fluorescence emission extracted in said step c).

Said or at least one said reversibly photoswitchable fluorescent species can be chosen from: a photochromic fluorescent protein; and a complex of a biomolecule, such as, for example, an aptamer or a protein, with a fluorogenic probe.

Said sample can comprise biological material.

Another subject of the invention is a fluorescence microscopy method implementing such a detection method.

Another subject of the invention is an optical remote sensing method implementing such a detection method.

According to embodiments of the invention:

said sample can comprise a living organism, and at least one element chosen from the presence and the concentration of one said reversibly photoswitchable fluorescent species (P) can be measured from the component of the intensity of said fluorescence emission extracted in said step c) without performing any sampling on said living organism.

said illuminating light (FEX) is emitted in a direction and said periodic modulation of said illuminating light (FEX) is implemented by a modulation of said direction of emission of said illuminating light (FEX).

According to another embodiment, the invention is a method in which said illuminating light (FEX) comprises a part of the daylight and in which said part of the daylight participates in the light intensity received by said reversibly photoswitchable fluorescent species (P) by remaining less than or equal to said intensity $I^0$.

BRIEF DESCRIPTION OF THE DRAWINGS

Other features, details and advantages of the invention will emerge on reading the description given with reference to the attached figures given by way of example, in which.

DETAILED DESCRIPTION

Figure 1:
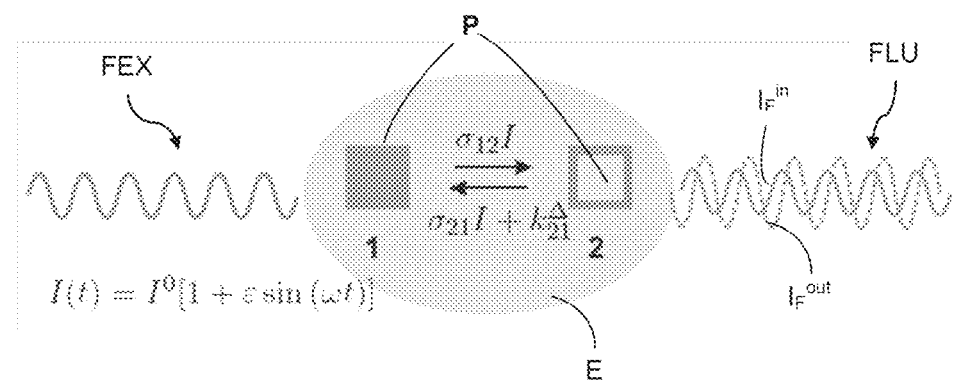
FIG. 1 illustrates the general principle of a method according to an embodiment of the invention.

As illustrated in FIG. 1, a detection method according to the invention comprises the illumination of a sample E, containing a reversibly photoswitchable fluorescent species P, by a periodically modulated excitation light beam FEX. The nonlimiting example of FIG. 1 considers the case of an excitation beam modulated sinusoidally at an angular frequency $\omega$, the intensity of which is given by $$I(t)=I_0[1+\varepsilon \sin(\omega t)]$$

in which $I^0$ is the average intensity and $\varepsilon \leq 1$ is the modulation amplitude. More generally, it will be possible to modulate the intensity of the excitation beam with any periodic function, the frequency of which is indicated by $f=1/T$ (T being the period; in the case of a sinusoidal modulation $f=\omega/2\pi$). The use of a modulation by a strobe function (rectangular wave, of any duty cycle) is particularly advantageous because of its simplicity of implementation. The modulation can also be obtained by periodically displacing an illuminating beam, for example in the context of a scanning microscopy observation; in effect, if a localized region of a sample (for example a chamber or a duct of a microfluidic device) is considered, a periodic displacement of an illuminating beam modifies the illumination in a way similar to a periodic modulation of the intensity of said beam.

The excitation beam FEX is preferably substantially monochromatic, that is to say that its spectrum exhibits a single intensity maximum, and/or a spectral width not greater than 50 nm.

The reversibly photoswitchable fluorescent species exhibits two different states that can be exchanged under the action of light. It can be a photochromic fluorescent species, or any other system whose dynamic behavior can be reduced to an exchange between two states under the action of the light; these states can correspond to different stereochemical configurations of a molecule, to a bonded/non-bonded state of a complex, etc. In FIG. 1, the first state—thermodynamically more stable—is indicated by 1 and represented by a solid square; the second state—thermodynamically less stable—is indicated by 2 and represented by a hollow square. These two states have different brightnesses. In the interests of simplicity, and by way of nonlimiting example, it can be considered that only the state 1 is significantly fluorescent.

The wavelength of the excitation beam, $\lambda$, allows for both the excitation of the fluorescence emission of the states 1 and 2, and also the switching from the state 1 to the state 2 and vice versa. Thus, in the case of illumination with a constant intensity I:

the state 1 is switched to the state 2 with a kinetic constant $\sigma_{12}I$, $\sigma_{12}$ being the effective cross section of photoswitching from the state 1 to the state 2;

the state 2 is switched to the state 1 with a kinetic constant $\sigma_{21}I+k^\Delta_{21}$, $\sigma_{21}$ being the effective cross section of photoswitching from the state 2 to the state 1 and $k^\Delta_{21}$ being the kinetic constant of thermal relaxation from the state 2 to the state 1.

The sample—and more specifically the species P that it contains—illuminated by the modulated excitation beam FEX, emits an emission of fluorescence FLU, the intensity of which is, again, modulated and can be divided into:

a component in phase with the excitation beam, indicated in the figure by $I_F^{in}$; and a component in quadrature with the excitation beam, indicated in the figure by $I_F^{out}$.

The present inventors found that it is possible to choose the average intensity $I^0$ of the illuminating beam and its modulation frequency f so as to maximize the amplitude of the component in quadrature of the fluorescence emission. The optimal values of the parameters $I^0$ and f which maximize this amplitude depend on the parameters $\sigma_{12}$, $\sigma_{21}$, $k^\Delta_{21}$ and on the reversibly photoswitchable fluorescent species considered. Thus, an excitation beam optimizing the amplitude of the component in quadrature of the emission of a target reversibly photoswitchable fluorescent species will not optimize that of other fluorescent species (reversibly photoswitchable or not) that may be present in the sample. A selective detection is thus obtained by dynamic contrast.

One advantageous feature of the invention is that the optimal values of the parameters $I^0$ and f can be calculated from the dynamic properties of the species to be detected, and more particularly $\sigma_{12}$, $\sigma_{21}$ and $k^\Delta_{21}$. There is therefore no need to use an iterative optimization, by tests, as in certain prior art techniques. Moreover, the optimal values of $I^0$ and f can be determined analytically.

Another advantage of the invention is that the selective detection can be quantitative. In other words, a calibration makes it possible to determine the concentration of the target reversibly photoswitchable fluorescent species from the amplitude of the component in quadrature of the fluorescent intensity.

The extraction of the amplitude of the component in quadrature of the fluorescent emission does not pose any particular difficulty. It can be done, for example, by lock-in detection or by analysis of the Fourier transform of the fluorescence intensity. Similarly, the modulation of the excitation beam can be obtained by known methods, for example the direct modulation of an illumination source or the use of a light modulator, electro-optical or mechanical.

Contrary to the techniques known from the prior art, there is no need to provide a plurality of excitation beams. A single illuminating beam—or a plurality of beams of the same wavelength and the same modulation, even a diffuse monochromatic illumination—can be used.

The theory on which the invention is based will now be explained in more detail using FIGS. 2A and 2B.

In the absence of illumination, the photoswitchable fluorescent species P exists almost exclusively in its most stable state, 1. When the system is illuminated with an intensity $I^0$, a photoswitching from the state 1 to the state 2 is observed, characterized by a rate constant:

$$k_{12}(t)=k_{12}^0=\sigma_{12}I^0 \quad (1)$$

and a switching—both thermal and photo-induced—from the state 2 to the state 1 characterized by a rate constant:

$$k_{21}(t)=k_{21}^0=\sigma_{21}I^0+k_{21}^\Delta \quad (2)$$

After a transient period, the duration of which is defined by the relaxation time $\tau_{12}^0 = 1/(k_{12}^0 + k_{21}^0)$, the system reaches a photostationary regime, characterized by the apparent photoisomerization constant $$K_{12}^0 = k_{12}^0/k_{21}^0 \quad (3)$$

In this regime, the concentrations of the states 1 and 2, denoted $1^0$ and $2^0$ respectively, are given by:

$$1^0 = P_{tot} - 2^0 = \frac{1}{1+K_{12}^0} P_{tot} \quad (4)$$

in which $P_{tot}$ is the total concentration of the species P. The intensity of the fluorescence emission $I_F(t)$ is given by:

$$I_F(t) = (Q_1 1 + Q_2 2) I(t) = I_F^0 = (Q_1 1^0 + Q_2 2^0) \quad (5)$$

in which $Q_1$ and $Q_2$ are the molecular brightnesses of the states 1 and 2 respectively, with $Q_1 \neq Q_2$.

The case of an illumination modulated sinusoidally at the angular frequency $\omega$ and with a modulation amplitude $\varepsilon$ is now considered:

$$I(t) = I_0[1 + \varepsilon \sin(\omega t)] \quad (6)$$

if $\varepsilon \ll 1$ then, to the first order:

$$k_{12}(t) = \sigma_{12} I^0 [1 + \varepsilon \sin(\omega t)]$$

$$k_{21}(t) = \sigma_{21} I^0 [1 + \varepsilon \sin(\omega t)] + k_{21}^\Delta \quad (7)$$

It should be noted that this hypothesis $\varepsilon \ll 1$ is in no way essential to the implementation of the invention, but simplifies the analytical development.

In other words, the invention can be implemented with a "strong" amplitude modulation ($\varepsilon$ close to 1) by retaining the values of the parameters $I^0$ and $\omega$ supplied below which then optimize the amplitude of the 1st order term in quadrature of the modulation of the concentrations in 1 and 2.

Beyond the relaxation time $\tau_{12}^0$, the system enters into a steady-state forced regime, in which the concentrations of the two states i (i=1 or 2) have the value:

$$i(t) = i^0 + \varepsilon[i^{1\,sin} \sin(\omega t) + i^{1\,cos} \cos(\omega t)] \quad (8)$$

in which $i^0$ is the concentration of i in the steady-state state associated with the photon flux $I^0$ whereas $\varepsilon i^{1\,sin}(\omega t)$ and $\varepsilon i^{1\,cos} \cos(\omega t)$ are the terms in phase and in quadrature oscillating at the angular frequency $\omega$. It can be demonstrated that:

$$1^{1sin} = -2^{1sin} = \rho_{12}^0 \tau_{12}^0 p_{21}^\Delta \frac{1}{1+(\omega\tau_{12}^0)^2} \quad (9)$$

and $$1^{1cos} = -2^{1cos} = \rho_{12}^0 \tau_{12}^0 p_{21}^\Delta \frac{\omega\tau_{12}^0}{1+(\omega\tau_{12}^0)^2} \quad (10)$$

in which $\rho_{12}^0 = k_{12}^0 1^0 = k_{21}^0 2^0$ and $p_{21}^\Delta = k_{21}^\Delta/(\sigma_{21} I^0 + k_{21}^\Delta)$.

The intensity of the fluorescence emission $I_F(t)$ then becomes:

$$I_F(t) = I_F^0 + I_F^{in} \sin(\omega t) + I_F^{out} \cos(\omega t) \quad (11)$$

with:

$$I_F^{in} = \varepsilon[(Q_1 1^0 + Q_2 2^0) + (Q_1 - Q_2) 1^{1\,sin}] I^0 \quad (12)$$

$$I_F^{out} = \varepsilon(Q_1 - Q_2) 1^{1\,cos} I^0 \quad (13)$$

By dividing by the average value $I_F^0$, the normalized fluorescence emission is obtained:

$$I_{F,norm}(t) = \frac{I_F(t) - I_F^0}{I_F^0} = (1+\alpha^{in})\varepsilon \sin(\omega t) + \alpha^{out} \varepsilon \cos(\omega t) \quad (14)$$

in which $\alpha^{in}$ and $\alpha^{out}$ are the amplitudes of the components in phase and in quadrature, respectively, defined by: $\alpha^{in} (Q_1-Q_2) 1^{1\,sin}/A^0$ and $\alpha^{out} = (Q_1-Q_2) 1^{1\,cos}/A^0$ with $A^0 = Q_1 1^0 + Q_2 2^0$.

For a fixed average illumination intensity, $I^0$, the triplet of parameters $(\sigma_{12}, \sigma_{21}, k_{21}^\Delta)$ characterizing the reversibly photoswitchable fluorophore P gives two equivalent sets of dynamic parameters: $(k_{12}^0, k_{21}^0)$ and $(K_{12}^0, \tau_{12}^0)$; this second set is selected to characterize the dynamics of the system. The terms $1^{1\,sin}$ and $1^{1\,cos}$, on which the components in phase and in quadrature of the fluorescence intensity depend, can then be expressed by:

$$1^{1sin} = -p_{21}^\Delta \frac{K_{12}^0}{(1+K_{12}^0)^2} \frac{1}{1+(\omega\tau_{12}^0)^2} P_{tot} \quad (15)$$

and $$1^{1cos} = p_{21}^\Delta \frac{K_{12}^0}{(1+K_{12}^0)^2} \frac{\omega\tau_{12}^0}{1+(\omega\tau_{12}^0)^2} P_{tot} \quad (16)$$

Figure 2A:
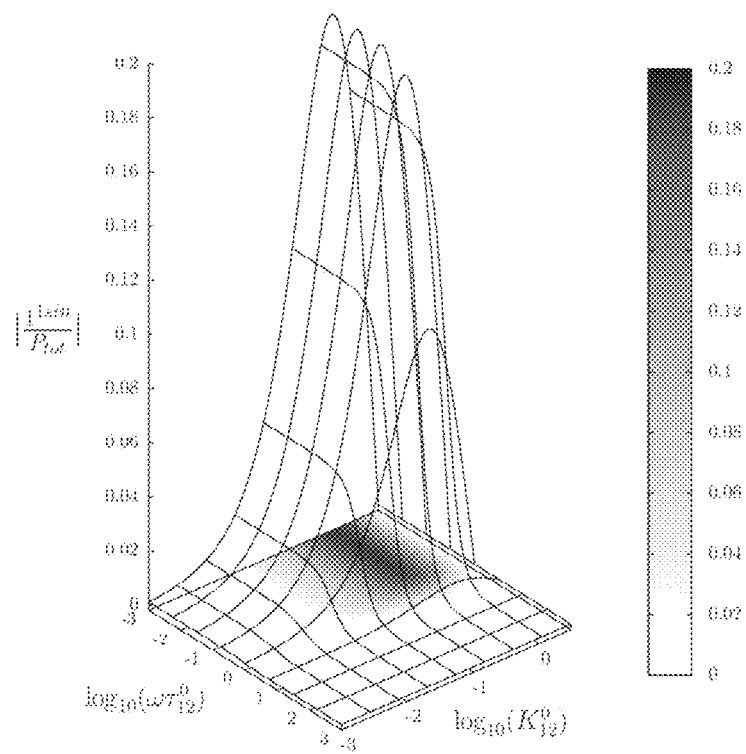
FIGS. 2A and 2B are graphs illustrating how the phase and quadrature components of the fluorescence intensity depend on the dynamic parameters of a reversibly photoswitchable fluorescent species.
Figure 2B:
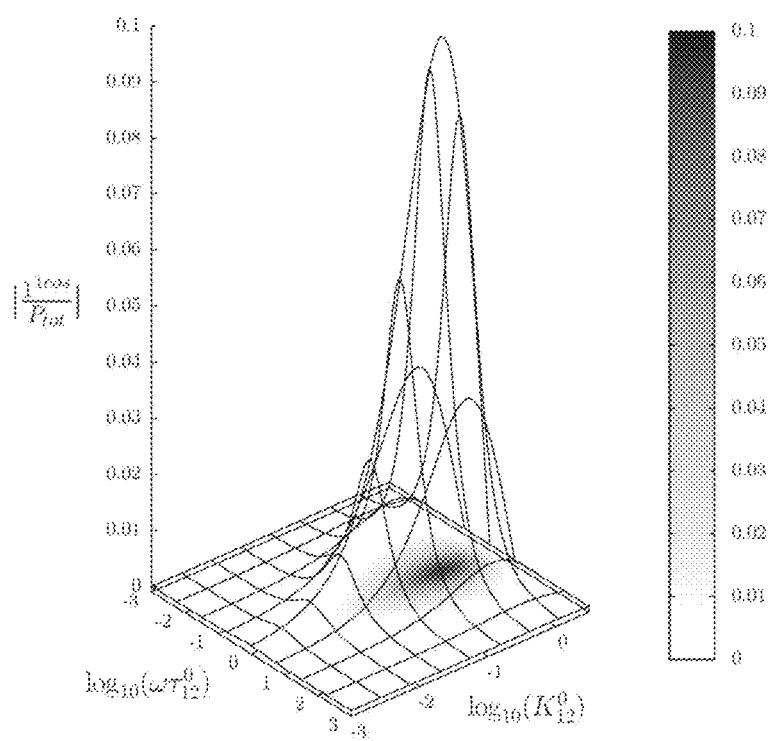

FIGS. 2A and 2B respectively illustrate the dependence of the normalized amplitude in phase $|1^{1\,sin}/P_{tot}|$ and of the normalized amplitude in quadrature $|1^{1\,sin}/P_{tot}|$ as a function of $K_{12}^0$ and $\omega\tau_{12}^0$ (expressed in logarithmic units). It can be noted that $1^{1\,cos}$—and therefore the component in quadrature $I_F^{out}$ of the fluorescent emission intensity—exhibits a well-defined maximum, which is not the case with $1^{1\,sin}$. This maximum is centered on the point:

$$K_{12}^0 = \frac{\sigma_{12}}{\sigma_{12} + 2\sigma_{21}} \quad (17)$$

$$\omega\tau_{12}^0 = 1 \quad (18)$$

It is possible to choose the control parameters $(I^0, \omega)$ so as to satisfy these conditions. The value of $1^{1\,cos}$ and of $I_F^{out}$—is therefore maximal when:

$$I^0 = \frac{k_{21}^\Delta}{\sigma_{12} + \sigma_{21}} \quad (19)$$

and $$\omega = 2k_{21}^\Delta \quad (20)$$

or, equivalently:

$$f = k_{21}^\Delta/\pi. \quad (21)$$

Physically, the condition (19) on $I^0$ amounts to equalizing the kinetic constants of the thermal and photo-induced reactions, and the condition (20-21) on $\omega$ or f amounts to tuning the modulation frequency on the relaxation time $\tau_{12}^0$ to satisfy the resonance condition (18).

The use of a modulation signal of low amplitude is conducive to the derivation of simple analytic expressions. On the other hand, it makes it possible to generate only small variations of the signal from the species P because of the weak modulations, which represents a drawback for a reliable extraction of a first order response in phase quadrature. The response of a photoswitchable species P can be analyzed in the case of a wide amplitude modulation a to mitigate this drawback. As an extension of the preceding case, a sinusoidal modulation of wide amplitude α can first of all be considered, such that:

$$I(t)=I^0[1+\alpha \sin(\omega t)] \tag{22}$$

To calculate the time dependence of the concentrations in reversibly photoswitchable fluorescent species, it can first of all be considered that, in a more general case, the light intensity can be written in the form:

$$I(t)=I^0[1+\alpha h(\omega t)] \tag{24}$$

in which $h(\omega t)$ designates a periodic function of fundamental radial frequency $\omega$. The equation 24 can be used to develop the rate constants of the equations 1 and 2. By writing the expression of the concentrations as follows:

$$2=2^0+\alpha f(\omega t) \tag{25}$$

$$1=1^0-\alpha f(\omega t) \tag{26}$$

the system of differential equations governing the temporal evolution of the concentrations 1 and 2 becomes:

$$\frac{df(\theta x)}{dx} = -f(\theta x) + [a - bf(\theta x)]h(\theta x) \tag{27}$$

in which:

$$x = \frac{t}{\tau_{12}^0} \tag{28}$$

$$a = \rho_{12}^0 p_{21}^\Delta \tau_{12}^0 \tag{29}$$

$$b = \alpha(\sigma_{12} + \sigma_{21})I^0 \tau_{12}^0 \tag{30}$$

$$\theta = \omega \tau_{12}^0 \tag{31}$$

After the relaxation time $\tau_{12}^0$, a steady-state regime, in which $f(\theta x)$ is a periodic continuous function, is established. Unlike the case of a sinusoidal modulation of low amplitude, it is not possible to restrict the analysis of $f(\theta x)$ to the first order. The function $f(\theta x)$ must be developed in Fourier series:

$$f(\theta x) = a_0 + \sum_{n=1}^{+\infty} [a_n\cos(n\theta x) + b_n\sin(n\theta x)] \tag{32}$$

in which $a_n$ and $b_n$ designate the amplitudes of the nth components of the Fourier series. The terms $a_n$ and $b_n$ can be extracted from the equation 27 by identification of the amplitudes of the same order. It is thus possible to obtain the expression of the concentrations 1 and 2:

$$2 = 2^0 + \alpha\left\{a_0 + \sum_{n=1}^{+\infty} [a_n\cos(n\theta x) + b_n\sin(n\theta x)]\right\} \tag{33}$$

$$1 = 1^0 - \alpha\left\{a_0 + \sum_{n=1}^{+\infty} [a_n\cos(n\theta x) + b_n\sin(n\theta x)]\right\}. \tag{34}$$

Consequently, in steady-state regime, a modulation of wide amplitude of the illumination leads to the modulation of the concentrations 1 and 2 over an infinity of radial frequencies. The equations 33 and 34 can be transformed to reveal the amplitudes $i^{n,in}$ and $i^{n,out}$ of the terms in phase or in phase quadrature oscillating with the radial frequency $n\omega$. The concentration of i can be written:

$$i = i^0 + \alpha \sum_{n=1}^{+\infty} [i^{n,in}\sin(n\omega t) + i^{n,out}\cos(n\omega t)]. \tag{35}$$

The terms $i^0$, $i^{n,in}$ and $i^{n,out}$ are proportional to $P_{tot}$. Indeed the equation 27 can be transformed into $$\frac{df(\theta x)}{dx} + f(\theta x)[1 + bh(\theta x)] = ah(\theta x). \tag{36}$$

Neither b nor $h(\theta_x)$ depend on $P_{tot}$ (see equations 22, 23, 28-31). On the other hand, α is proportional to $P_{tot}$ (see equations 4 and 29). Since the derivation is linear, the equation 36 means that $f(\theta x)$ is proportional to $P_{tot}$. The system of equations giving access to $a_n$ and $b_n$ is linear. It can therefore be deduced that all the amplitudes $a_n$ and $b_n$ are individually proportional to $P_{tot}$. Finally, the equations 33 to 35 can be used to deduce that the $i^0$, $i^{n,in}$ and $i^{n,out}$ are proportional to $P_{tot}$. It has been demonstrated previously that, in the case of a sinusoidal modulation of the light of small amplitude, $2^{1,out}$ is optimal when the resonance conditions of the equations 19 and 21 are fulfilled. In the absence of an analytical expression for $2^{1,out}$, such conclusions cannot be drawn in the case of a periodic light modulation of strong amplitude. Their relevance has been assessed by means of numerical calculations.

As an example of embodiment of the invention, the case of the sinusoidal modulation of wide amplitude was analyzed. More particularly, the dependence $1^{1,out}=-2^{1,out}=-a_1$ was analyzed on the control parameters ω and $I^0$. To this end, the 2n+1 unknown parameters $(a_0, \ldots, a_n, b_n)$ are found by truncation of the development in Fourier series (equation 32) for the increasing orders of n.

Figure 3:
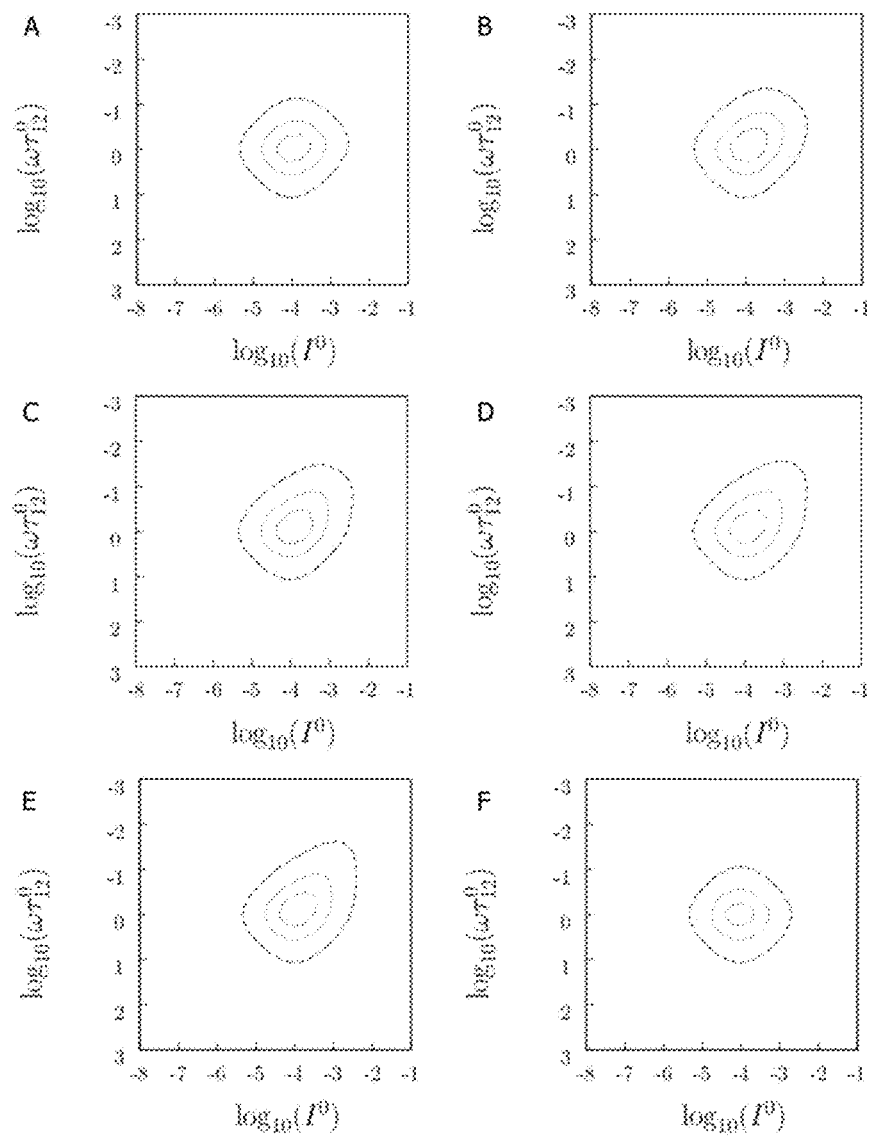
FIGS. 3A, 3B, 3C, 3D, 3E and 3F are graphs illustrating the result of calculations of the amplitude normalized in phase quadrature, as a function of different control parameters.

FIG. 3 displays the dependence of the normalized amplitude $|1_{norm}^{1,out}|=|1^{1,out}/P_{tot}|$, on the light flux $I^0$ (in ein·s$^{-1}$·m$^{-2}$) and the dimensionless radial frequency $\omega\tau_{12}^0$ when α=1. The numerical calculation is performed upon truncating the Fourier series $f(\theta x)$ at the $1^{st}$, $2^{nd}$, $3^{rd}$, $4^{th}$ and $5^{th}$ order respectively for the panels A, B, C, D and E. The panel F displays the dependence of the normalized amplitude on the same variables, observed in a regime of low amplitude modulation. The markers correspond to the isodensity curves (0.01 for the dashes, 0.03 for the dots and 0.05 for the dashes). The truncation of the Fourier series of the function $f(\theta x)$ to the $5^{th}$ order (n=5) is sufficient to observe a convergence: the dependence of $|1_{norm}^{1,out}|$ on $I^0$ and ω does not change significantly beyond n=5. $|1_{norm}^{1,out}|$ exhibits an optimum in space ($I^0$, ω), for which the position and the amplitude are very close to those observed in the case of a sinusoidal modulation of low amplitude. The error made by taking the analytical expression, valid only for the modulation of low amplitude, is less than 20%, whatever the amplitude of α used. Such an error is of the order of the experimental error by setting the average light intensity and the radial frequency at their resonance values, $I^{O,R}$ and $\omega^R$.

If, instead of considering a single reversibly photoswitchable fluorescent species, the interest is focused on a sample containing a plurality of such species, exhibiting different dynamic parameters but superimposed or close absorption/emission bands (included in the spectral width of the illuminating light), the intensity in quadrature will exhibit a plurality of local maxima, one for each said species.

Figure 4:
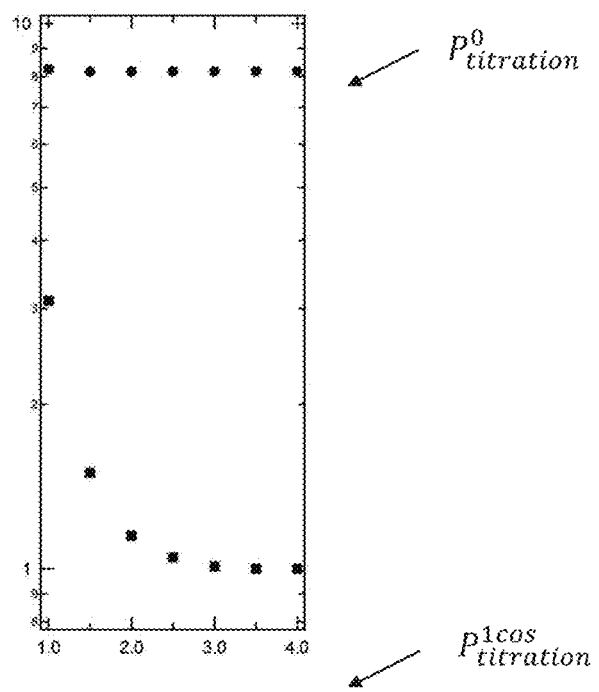
FIG. 4 is a graph illustrating the application of a method according to an embodiment of the invention to the determination of the concentration of a reversibly photoswitchable fluorescent species.

FIG. 4 highlights the selectivity of detection according to the invention, as well as its quantitative nature.

In this figure, the case is considered of a sample containing nine reversibly photoswitchable fluorescent species, having a same concentration, identical absorption and emission wavelengths, and a state 1 of the same brightness (the state 2 is considered as non-fluorescent, with no loss of generality): one target species and eight interfering species. In the space $$\left( \log_{10} \frac{k_{21,X}^{\Delta}}{k_{21}^{\Delta}}, \log_{10} \frac{\sigma_{12,X}}{\sigma_{12}}, \log_{10} \frac{\sigma_{21,X}}{\sigma_{21}} \right)$$

("X" identifies the interfering species, the parameters without this index referring to the target species), the interfering species form a cube of edge "n", with the target species at the center. Seven different cases are considered, corresponding to the following values of "n": 1; 1.5; 2; 2.5; 3; 3.5; 4.

If an attempt is made to titrate the target species by fluorescence detection by using an illumination of constant intensity, the measurement is strongly affected by the interfering species. It is found, more precisely, and independently of the value of "n", that:

$$P_{titration}^{0} = P_{tot} + \sum_{X} \frac{(1_X^0 / X_{tot})}{(1^0 / P_{tot})} X_{tot} \qquad (37)$$

in which $P_{titration}^{0}$ is the measured concentration of the target, extracted from the quantification of the average fluorescence intensity, $P_{tot}$ is its real concentration, $X_{tot}$ the total concentration of the interfering species X, $1^0$ and $1^0_X$ the steady-state concentrations under illumination at constant intensity $I^0$ of the target and of the interfering species X, respectively. As the graph of FIG. 4 shows, the concentration is over-estimated by a factor greater than 8.

If, however, a modulated illumination is used together with a detection in quadrature of the fluorescence, the following expression is obtained:

$$P_{titration}^{1cos} = P_{tot} + \sum_{X} \frac{(1_X^{1cos} / X_{tot})}{(1^{1cos} / P_{tot})} X_{tot} \qquad (38)$$

in which $P_{titration}^{1\ cos}$ is the measured concentration of the target, extracted from the analysis of the response in quadrature, and $1^{1\ cos}$ and $1_X^{1\ cos}$ are the amplitudes of the components in quadrature of the concentrations of the states 1 of the target and of the interfering species X.

When the modulation frequency and the intensity of the illumination are optimized for the detection of the target species, $1^{1\ cos}/P_{tot}$ is very much greater than $1_X^{1\ cos}/X_{tot}$. The graph of FIG. 4 shows that $P_{titration}^{1\ cos}$ is closer to $P_{tot}$ when the parameter "n" is high. When the dynamic properties of the interfering species are sufficiently far apart from those of the target species (n≥2 in the example considered here), the overestimation that they cause is negligible. The selectivity obtained by virtue of the invention method therefore allows for a quantitative detection (titration) even in the presence of interfering species—provided that the latter exhibit dynamic parameters that are sufficiently different from those of the target species, which is generally the case, more so as most of the interfering fluorophores naturally present in the samples, notably biological, are not reversibly photoswitchable.

The results displayed in FIG. 4 were obtained by numerical simulation, by considering the following parameters: $\sigma_{12}=20.9$ m$^2$·mol$^{-1}$; $\sigma_{21}=6.8$ m$^2$·mol$^{-1}$; $k_{21}^{\Delta}=2.8\cdot10-3$ s$^{-1}$.

As a variant, it is possible to use two distinct excitation beams, with different wavelengths: each of the two beams, of different electromagnetic spectrum and light intensity, can impose different rate constants of the reactions linking the two states of the species P. One of the disadvantages in the use of two beams is complicating the implementation of the detection method. On the other hand, it does advantageously make it possible to overcome the limitation on the acquisition rate linked to the thermal relaxation from the state 2 to the state 1 in the case of the use of a single light beam.

In this particular embodiment of the invention, the species P is illuminated by a light of intensity I(t), comprising components $I_1(t)$ and $I_2(t)$, respectively of wavelengths $\lambda_1$ and $\lambda_2$. The system with two states described previously then has the following rate constants:

$$k_{12}(t)=\sigma_{12,1}I_1(t)+\sigma_{12,2}I_2(t) \qquad (39)$$

$$k_{21}(t)=\sigma_{21,1}I_1(t)+\sigma_{21,2}I_2(t)+k_{21}^{\Delta} \qquad (40)$$

in which: $\sigma_{12,1}I_1(t)$, $\sigma_{12,2}I_2(t)$, $\sigma_{21,1}I_1(t)$, $\sigma_{21,2}I_2(t)$ and $k_{21}^{\Delta}$ are respectively the photochemical and thermal contributions of the rate constants. In this case, the effective molecular sections for the photoisomerization $\sigma_{12,1}$ and $\sigma_{21,1}$ (to $\lambda_1$), $\sigma_{12,2}$ and $\sigma_{21,2}$ (to $\lambda_2$), and the thermal relaxation constant $k_{21}^{\Delta}$ fully define the behavior of a photoswitchable species P.

In a particular embodiment of the invention, this system is used with an illumination with the wavelength $\lambda_1$, of sinusoidal periodic intensity oscillating about the average value $I_1^0$ at a radial frequency $\omega_1$ and with a small oscillation amplitude $\varepsilon I_1^0$ ($\varepsilon<<1$), on which is superimposed an illumination of wavelength $\lambda_2$, with $\lambda_1 \neq \lambda_2$, of constant intensity $I_2^0$. The following expression then applies:

$$I(t)=I_1^0[1+\varepsilon \sin(\omega t)]+I_2^0 \qquad (41)$$

By introducing:

$$k_{12,1}^0=\sigma_{12,1}I_1^0 \qquad (42)$$

$$k_{21,1}^0=\sigma_{21,1}I_1^0 \qquad (43)$$

$$k_{12,2}^0=\sigma_{12,2}I_2^0 \qquad (44)$$

$$k_{21,2}^0=\sigma_{21,2}I_2^0 \qquad (45)$$

the following expression can be written:

$$k_{12}(t)=k_{12,1}^0[1+\varepsilon \sin(\omega t)]+k_{12,2}^0 \qquad (46)$$

$$k_{21}(t)=k_{21,1}^0[1+\varepsilon \sin(\omega t)]+k_{21,2}^0+k_{21}^{\Delta}, \qquad (47)$$

and the system of differential equations governing the temporal evolution of the concentrations 1 and 2 is solved at the first order of this light perturbation. After the relaxation time $\tau_{12}^0$, a forced and steady-state regime is established, in which the concentration:

$$i = i^0 + \varepsilon i^1 \sin(\omega t - \phi_{12}) \tag{48}$$

in each species i (i=1 or 2) oscillates about an average value $i^0$ (which corresponds to the concentration of i in steady-state regime associated with the photon flux $I^0$; see equation 4) with the radial frequency $\omega$ but with a phase delay of $\phi_{12} = \arctan(\omega \tau_{12}^0)$. The amplitudes of the concentration modulations are given by:

$$2^1 = -1^1 = \frac{\rho_{12}^0 \tau_{12}^0 \Delta_{12}^0}{\sqrt{1 + (\omega \tau_{12}^0)^2}} \tag{49}$$

in which:

$$\rho_{12}^0 = k_{12}^0 1^0 = k_{21}^0 2^0 \tag{50}$$

and $$\Delta_{12}^0 = \frac{k_{12,1}^0}{k_{12,1}^0 + k_{12,2}^0} - \frac{k_{21,1}^0}{k_{21,1}^0 + k_{21,2}^0 + k_{21}^\Delta} \tag{51}$$

designates the rate of the reaction in steady-state regime and the contributions of the photochemical processes by the modulated light, to the transition from 1 to 2 and respectively from 2 to 1 by illuminating at $I^0$.

The concentrations i can also be written:

$$i(t) = i^0 + \varepsilon[i^{1,in} \sin(\omega t) + i^{1,out} \cos(\omega t)] \tag{52}$$

in which $\varepsilon i^{1,in} \sin(\omega t)$ and $\varepsilon i^{1,out} \cos(\omega t)$ are the terms oscillating in phase and in phase quadrature with the radial frequency $\omega$. The amplitudes $i^{1,in}$ and $i^{1,out}$ of the terms in phase and in phase quadrature are:

$$2^{1,in} = \tag{53}$$
$$-1^{1,in} = \rho_{12}^0 \tau_{12}^0 \Delta_{12}^0 \frac{1}{1 + (\omega \tau_{12}^0)^2} = \Delta_{12}^0 \frac{K_{12}^0}{(1 + K_{12}^0)^2} \frac{1}{1 + (\omega \tau_{12}^0)^2} P_{tot}$$

$$2^{1,out} = -1^{1,out} = \tag{54}$$
$$-\rho_{12}^0 \tau_{12}^0 \Delta_{12}^0 \frac{\omega \tau_{12}^0}{1 + (\omega \tau_{12}^0)^2} = -\Delta_{12}^0 \frac{K_{12}^0}{(1 + K_{12}^0)^2} \frac{\omega \tau_{12}^0}{1 + (\omega \tau_{12}^0)^2} P_{tot}$$

in which $\rho_{12}^0 \tau_{12}^0 = P_{tot}[K_{12}^0/(1+K_{12}^0)^2]$.

Since the fluorescent emission originates from the contributions of the species 1 and 2, the phase delay in the oscillating concentrations causes a phase delay in the oscillating fluorescent emission. The oscillating fluorescent emission is then:

$$I_F(t) = I_F^0 + I_F^{1,in} \sin(\omega t) + I_F^{1,out} \cos(\omega t) \tag{55}$$

in which the amplitudes $I_F^{1,in}$ and $I_F^{1,out}$ of the terms in phase and in phase quadrature are:

$$I_F^{1,in} = \varepsilon[(Q_1 1^0 + Q_2 2^0) I^1 + (Q_1 - Q_2) 1^{1,in} I^0] \tag{56}$$

$$I_F^{1,out} = \varepsilon(Q_1 - Q_2) 1^{1,out} I^0. \tag{57}$$

with $I^0 = I_1^0 + I_2^0$.

The embodiment of the invention using two distinct excitation beams differs from the embodiment of the invention using a single excitation beam in the limit at which the exchanges between the states 1 and 2 are essentially due to the photochemical contributions when using two beams.

Figure 5A:
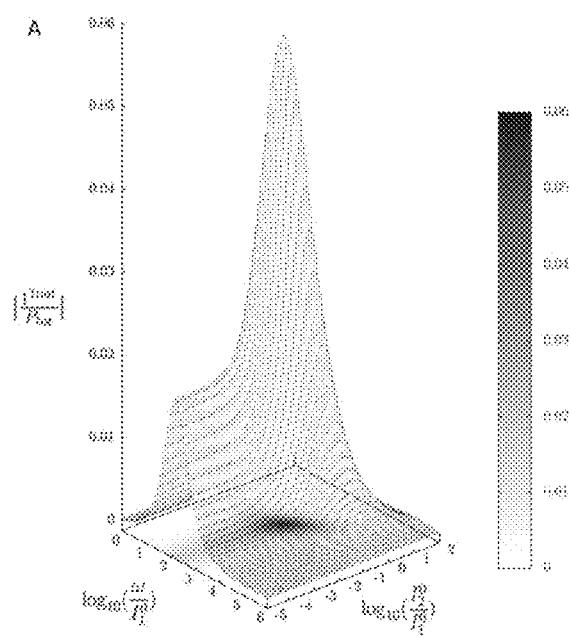
FIGS. 5A and 5B are graphs illustrating the calculations performed to optimize the detection in phase quadrature in the case of an excitation with two distinct light beams.
Figure 5B:
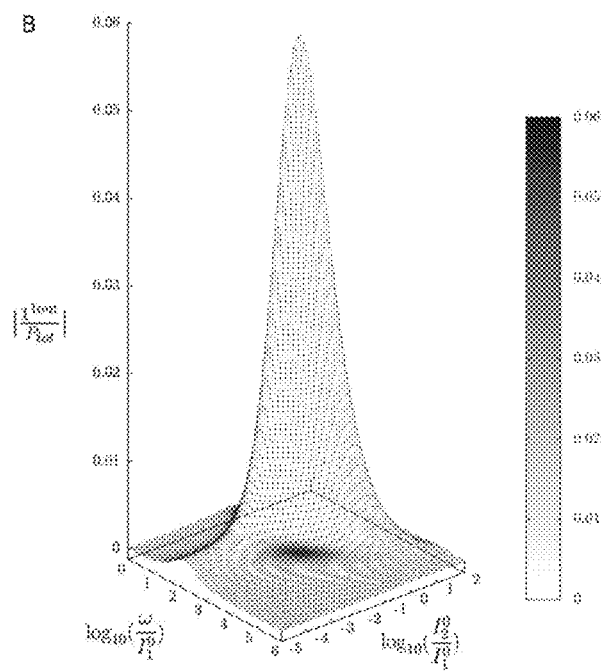

It is possible, when implementing the invention using two excitation beams, to calculate the control parameters to optimize the response in phase quadrature. The analysis is restricted to the intensity range $(I_1^0, I_2^0)$ such that $\sigma_{21,1} I_1^0 + \sigma_{21,2} I_2^0 \gg k_{21}^\Delta$. The panels A and B of FIG. 5 illustrate these calculations. In FIG. 5, the fluorescent species P used is Dronpa-2. It is characterized by the quintuplet of parameters $(\sigma_{12,1}, \sigma_{21,1}, \sigma_{12,2}, \sigma_{21,2}, k_{12}^\Delta)$ such that $\sigma_{12,1} \gg \sigma_{12,2}$ and $\sigma_{21,2} \gg \sigma_{21,1}$. Its normalized amplitude in phase quadrature $|\Delta 1_{norm}^{out}| = |1^{1,out}/\varepsilon P_{tot}|$ is displayed in FIG. 5 as a function of the control parameters $I_2^0/I_1^0$ and $\omega/I_1^0$.

$|\Delta 1_{norm}^{out}|$ shows a singular optimum when the following two resonance conditions are fulfilled:

$$\frac{I_2^0}{I_1^0} = \frac{\sigma_{12,1} + \sigma_{21,1}}{\sigma_{12,2} + \sigma_{21,2}} \tag{58}$$

$$\frac{f'}{I_1^0} = (\sigma_{12,1} + \sigma_{21,1})/\pi \tag{59}$$

The optimization of $1^{1,out}$ stems from the independent optimization of the terms $\rho_{12}^0 \tau_{12}^0 \Delta_{12}^0$ and $$\frac{\omega \tau_{12}^0}{1 + (\omega \tau_{12}^0)^2}$$

in the equation 54. $\rho_{12}^0 \tau_{12}^0 \Delta_{12}^0$ measures the composition deviation $\Delta_2^0$ of the steady-state regime $2^0$ after a light intensity jump of amplitude $\Delta I_1^0 = \varepsilon I_1^0$. This component is maximized when the photochemical reactions induced by the two light sources occur at the same rate. The second optimized term, $\omega \tau_{12}^0/[1+(\omega \tau_{12}^0)^2]$, is maximized by adjusting the radial frequency $\omega$ with the exchange relaxation time $\tau_{12}^0$ such that $\omega \tau_{12}^0 = 1$. When $\omega \gg 1/\tau_{12}^0$, the exchange is slow compared to the light variations, and the species $\{1, 2\}$ does not have enough time to respond. The terms $i^{1,in}$ and $i^{1,out}$ then disappear. Conversely when $\omega \ll 1/\tau_{12}^0$ $i^{1,out}$ is cancelled out, the concentrations 1 and 2 then oscillate in phase with the light modulation.

The panel A of FIG. 5 displays the normalized amplitude of the oscillations in phase quadrature $|\Delta 1_{norm}^{out}| = |1^{1,out}/\varepsilon P_{tot}|$ in the case where $$I_1^0 = 10 \frac{k_{21}^\Delta}{\sigma_{12,1} + \sigma_{21,1}}.$$

The panel B of FIG. 5 displays the normalized amplitude of the oscillations in phase quadrature $|\Delta 1_{norm}^{out}| = |1^{1,out}/\varepsilon P_{tot}|$ in the case where $$I_1^0 = 100 \frac{k_{21}^\Delta}{\sigma_{12,1} + \sigma_{21,1}}.$$

In a particular embodiment of the invention, it is possible to use two distinct light beams, in which the intensity of one of the light beams is modulated with a large amplitude relative to the average value of its intensity, as in the case of illumination with a single light source.

The invention has also been validated experimentally.

Figure 6:
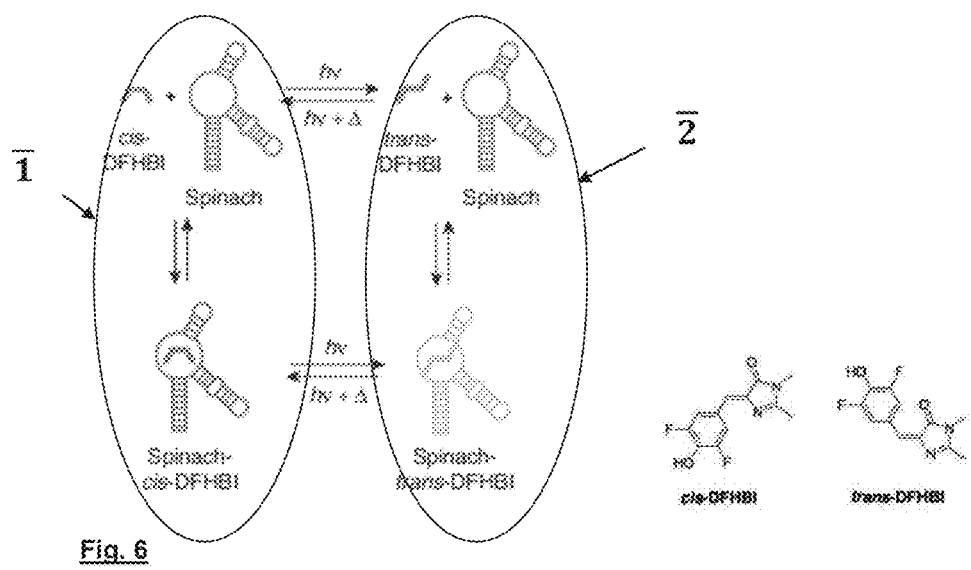
FIG. 6 illustrates the application of a method according to an embodiment of the invention to the detection of the reversibly photoswitchable fluorescent complex "Spinach"
Figure 7:
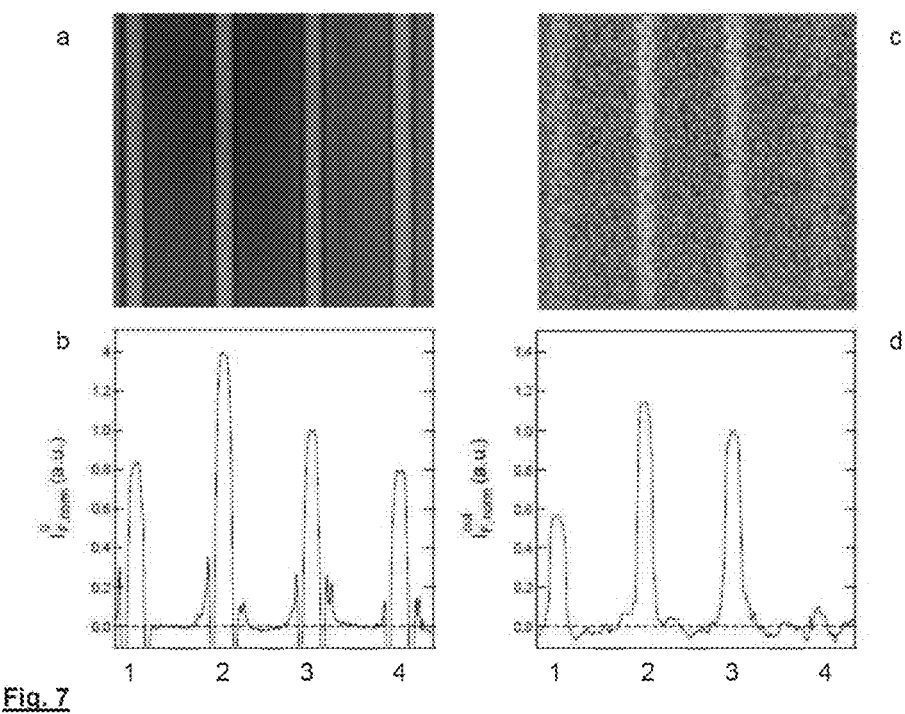
FIG. 7 illustrates the application of a method according to an embodiment of the invention to the selective imaging of a mixture comprising the reversibly photoswitchable fluorescent complex "Spinach" and an interfering fluorophore in a microfluidic device.

A first validation, illustrated by FIG. 7, uses, as reversibly photoswitchable fluorescent species, the "Spinach-DFHBI" system, illustrated by FIG. 6.

"Spinach" is an aptamer capable of complexing small molecules. DFHBI is a fluorogen that can be complexed by "Spinach" and that can exist in the form of two isomers, cis and trans. The system therefore exists in four states:

free cis-DFHBI, indicated by $1_{free}$;
free trans-DFHBI, indicated by $2_{free}$;
complexed cis-DFHBI, indicated by $1_{bound}$;
complexed trans-DFHBI, indicated by $2_{bound}$.

The bound (complexed) states are fluorescent, contrary to the free states, and in particular the state $1_{bound}$ is both more stable and brighter than the state $2_{bound}$. The trans-cis (2→1) isomerization reaction occurs both thermally (symbol "Δ" in FIG. 6) and under the effect of an illumination (symbol "hv"), whereas the cis-trans (1→2) reaction is exclusively photoinduced (symbol "hv").

In the low illumination regime, the photoisomerization reactions are slow compared to the complexation/decomplexation reactions. Consequently, the pairs of states ($1_{free}$; $1_{bound}$) and ($2_{free}$; $2_{bound}$) can be considered as virtual states $\overline{1}$ and $\overline{2}$. Thus, the "Spinach—DFHBI" system can be considered as a reversibly photoswitchable fluorescent species, and the theory explained above applies.

A microfluidic device comprising four channels (depth 200 µm, width 50 µm) was used as sample; the channels 1 to 4 of the device were filled with the following solutions:

1: (Spinach 250 nM, DFHBI 2.5 µM)+75 nM Fluorescein;
2: (Spinach 500 nM, DFHBI 5 µM)+50 nM Fluorescein;
3: (Spinach 500 nM, DFHBI 5 µM) only;
4: Fluorescein 100 nM only.

The system (Spinach—DFHBI) models the target species and Fluorescein models an interfering fluorophore.

The panel "a" of FIG. 7 shows a fluorescence image of this microfluidic device recorded, by means of a microscope, in the presence of a constant illumination; the panel "b" shows the corresponding normalized fluorescence intensity, $I^0_{F,norm}$, integrated over the length of the channels imaged. The panels "c" and "d" correspond to the case of a modulated illumination and of a detection in quadrature, in optimal conditions for the detection of the target species.

It can be seen in the panel "d" that the fluorescence intensities $I^{out}_{F,norm}$, measured in accordance with the invention, are substantially proportional to the concentrations of (Spinach—DFHBI): two times greater in the channels 2 and 3 than in the channel 1 and zero in the channel 4. By contrast, the measurements performed in constant illumination (panel "b") are considerably perturbed by the presence of Fluorescein (intensity in the channel 4 substantially equal to that in the channel 1, while the target species is absent).

Figure 8:
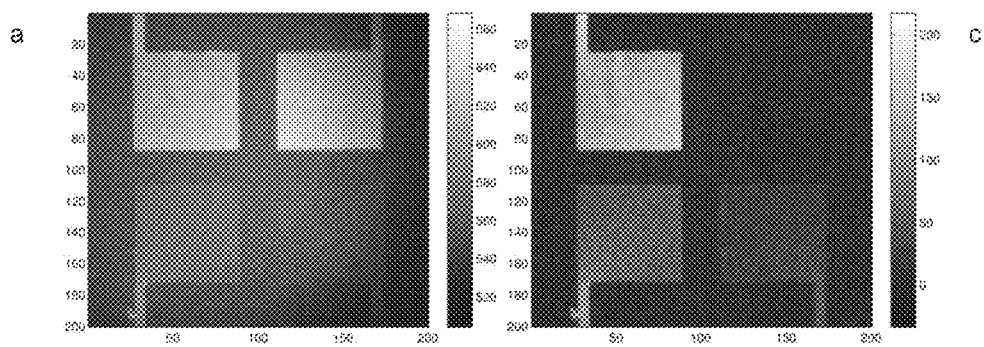
FIG. 8 illustrates the application of a method according to an embodiment of the invention to the selective imaging of a mixture comprising the reversibly photoswitchable fluorescent protein "Dronpa-2" and an interfering fluorophore in a microfluidic device.

A second validation, illustrated by FIG. 8, uses, as reversibly photoswitchable fluorescent species, the protein "Dronpa-2".

A microfluidic device comprising four square chambers (length×width×thickness=400×400×20 µm³) was used as sample; the chambers 1 to 4 of the device were filled with the following solutions:

1: (Dronpa-2 20 µM, BSA 100 µM) (top left);
2: Fluorescein 1 µM only (top right);
3: (Dronpa-2 10 µM, BSA 100 µM) (bottom left);
4: (Dronpa-2 5 µM, BSA 100 µM) (bottom right).

The Dronpa-2 system models the target species and the Fluorescein models an interfering fluorophore.

The panel "a" of FIG. 8 shows a fluorescence image of this microfluidic device acquired, by means of a microscope, in the presence of a constant illumination. The panel "b" corresponds to the case of a modulated illumination and of a detection in quadrature, in optimal conditions for the detection of the target species.

It can be seen in the panel "b" that the fluorescence intensities $I^{out}_{F,norm}$, measured in accordance with the invention, are substantially proportional to the concentrations of Dronpa-2: a ratio 4 and 2 for the chambers 1 and 3 compared to the chamber 4. It can also be seen that the fluorescence intensity $I^{out}_{F,norm}$ is close to zero in the square containing only the Fluorescein.

Obviously, reversibly photoswitchable fluorescent species other than those mentioned above can be used to implement the invention.

Figure 9:
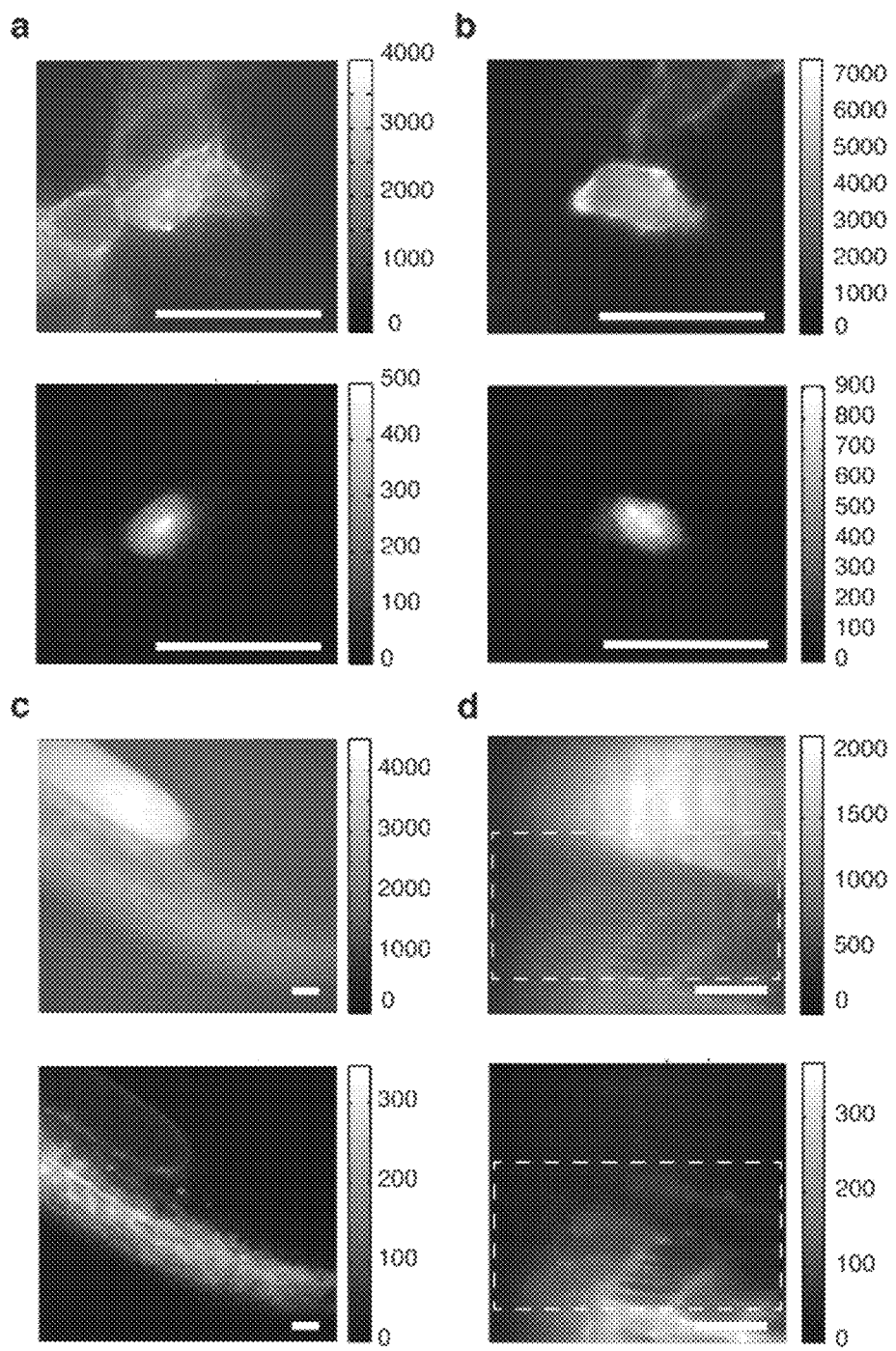
FIG. 9 illustrates the application of a method according to an embodiment of the invention to the selective imaging of biological material expressing the reversibly switchable fluorescent protein "Dronpa-3"

FIG. 9 illustrates the application of a method according to an embodiment of the invention to the selective imaging of biological material expressing the reversibly switchable fluorescent protein "Dronpa-3". The panels "a" and "b" of FIG. 9 illustrate the selective imaging of "Dronpa-3" expressed in mammal cells. Each panel displays two images, one corresponding to a photograph taken in epifluorescence and the other corresponding to a photograph taken in selective imaging of HEK293 cells expressing both "Dronpa-3", which is a reversibly photoswitchable fluorescent species, in the nucleus, and "EGFP", which is not a reversibly photoswitchable fluorescent species, in their membrane. The panel "a" displays a fixed cell whereas the panel "b" displays a living cell, the image of which is taken after a period of modulation of the light signal. The scale bar is 50 µm.

The panels "c" and "d" illustrate the selective imaging of "Dronpa-3" in zebra fish embryos taken 24 hours after fertilization, and expressing "lifeact-Dronpa-3", targeting actin. Similarly, each panel displays two images, one corresponding to a photograph taken in epifluorescence and the other corresponding to a photograph taken in selective imaging. The panel "c" displays an image in which the modulation of the illumination amplitude is sinusoidal and of large amplitude (α=90%), and in which the control parameters are set to the resonance of "Dronpa-3". The panel "d" displays an image in which a square wave modulation of illumination of high amplitude (α=90%) has been applied and in which the control parameters are set to the resonance of "Dronpa-3". The panel "c" displays images of epifluorescence, whereas the panel "d" displays images acquired in single plane illumination microscopy (SPIM). In the panel "d", the dotted outline white rectangle indicates the thinner part of the excitation light plane. The selective imaging here makes it possible to observe the actin network more specifically than in epifluorescence. The images of the panels "a", "b" and "c" of FIG. 9 are taken at 37° C. and the image of the panel "d" is taken at 20° C. The scale bar is 50 µm.

Figure 10:
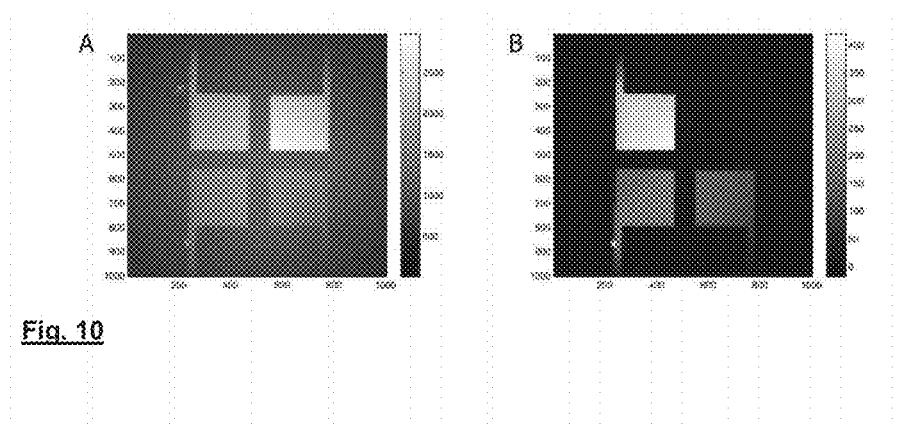
FIG. 10 illustrates the application of a method according to an embodiment of the invention using two excitation beams to the selective imaging of a mixture comprising the reversibly photoswitchable fluorescent protein "Dronpa-2" and an interfering fluorophore in a microfluidic device.

Another validation, illustrated by FIG. 10, uses, as reversibly photoswitchable fluorescent species, the protein "Dronpa-2" which is excited by two distinct light beams, at substantially monochromatic wavelengths of 480 nm and 405 nm. One of the beams (λ=405 nm) illuminates with constant intensity and the other (λ=480 nm) with a large amplitude intensity modulation.

A microfluidic device comprising four square chambers (length×width×thickness=400×400×20 µm³) was used as sample; the chambers 1 to 4 of the device were filled with the following solutions:

1: (Dronpa-2 20 μM, BSA 100 μM) (top left);
2: Fluorescein 1 μM only (top right);
3: (Dronpa-2 10 μM, BSA 100 μM) (bottom left);
4: (Dronpa-2 5 μM, BSA 100 μM) (bottom right).

The Dronpa-2 system models the target species and the Fluorescein models an interfering fluorophore.

The panel "A" of FIG. 10 shows an image of fluorescence of this microfluidic device acquired, by means of a microscope, in the presence of a constant illumination. The panel "B" corresponds to the case of a detection in quadrature, in optimal conditions for the detection of the target species.

It can be seen in the panel "B" that the fluorescence intensities $I^{out}_{F,norm}$, measured in accordance with the invention, are substantially proportional to the concentrations of Dronpa-2: a ratio 4 and 2 for the chambers 1 and 3 compared to the chamber 4. It can also be seen that the fluorescence intensity $I^{out}_{F,norm}$ is close to zero in the square containing only the Fluorescein.

Obviously, reversibly photoswitchable fluorescent species other than those mentioned above can be used to implement the invention.

Figure 11:
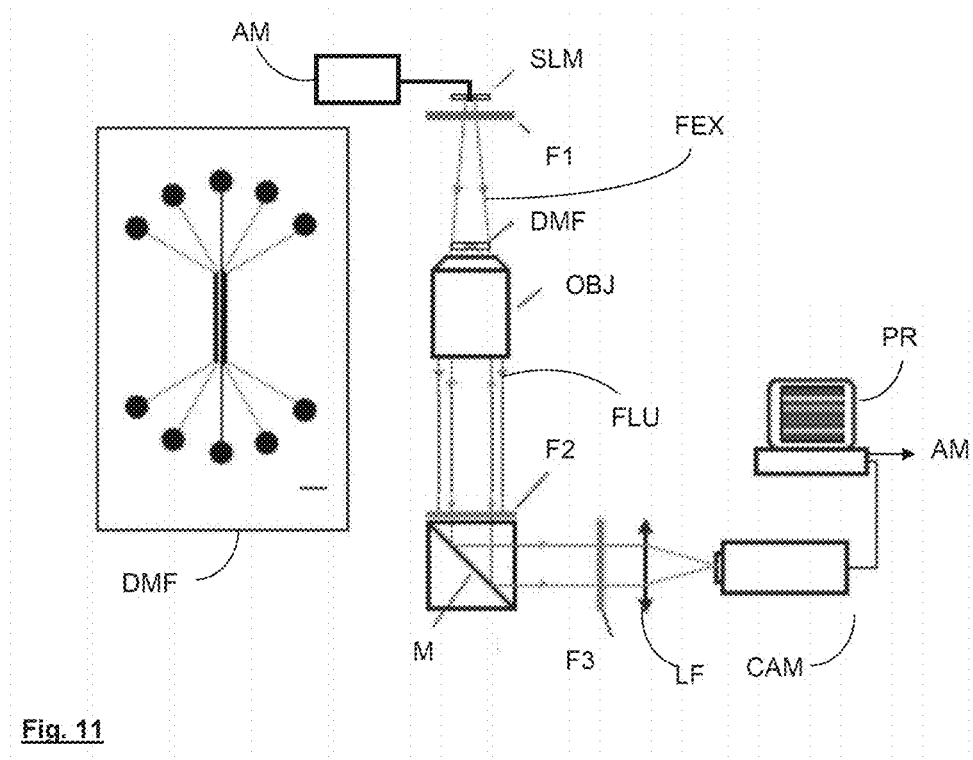
FIG. 11 schematically illustrates the experimental apparatus used to obtain FIG. 7.

FIG. 11 illustrates an apparatus for implementing a method according to an embodiment of the invention, of the type used to carry out some of the experimental validations described above. Such an apparatus, illustrated by way of nonlimiting example, comprises a light source SLM consisting of a strip of light-emitting diodes, powered by a power source AM. The modulation of the excitation light beam FEX generated by said source is obtained by modulation of the electrical power supply. Since the emission of the light-emitting diodes is wideband, the beam FEX is filtered by a first optical filter F1, before being directed onto a sample, consisting in this case of a microfluidic device DMF. The duly illuminated sample is observed, by its rear face, by an objective OBJ which collects the fluorescence emission and focuses it into a beam FLU. The latter is filtered (filters F2, F3) and directed, via a mirror M and a lens LF, to a camera CAM. A processor PR (in fact, a computer appropriately programmed) drives the power source AM and the camera CAM so as to perform a detection in quadrature as described above. To perform a simple detection or a titration, without imaging, the camera CAM can be replaced by a spot light sensor.

Figure 12:
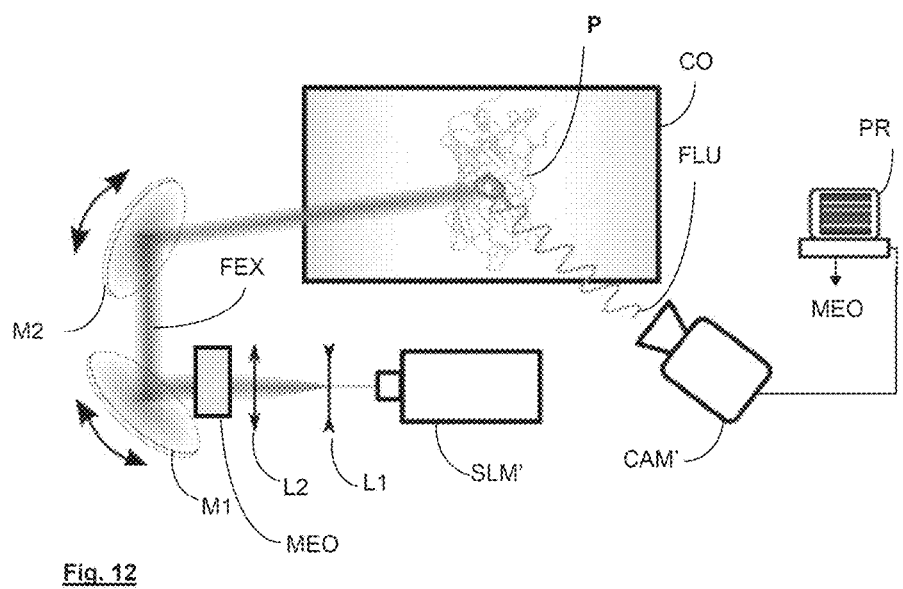
FIG. 12 schematically illustrates an apparatus that can be used in remote sensing applications according to an embodiment of the invention.

FIG. 12 illustrates an apparatus for implementing a method according to another embodiment of the invention, making it possible to remotely detect reversibly photoswitchable fluorescent probes in the environment. In such an application, the great selectivity made possible by the detection in quadrature is necessary to evidence the useful signal against the very intense background consisting of the ambient light.

In the apparatus of FIG. 12, the light source SLM' is a laser oscillator operating in continuous regime. The excitation beam FEX is expanded and collimated by two lenses L1, L2, then modulated by an electro-optical modulator MEO. Two steerable mirrors M1 and M2 are used to scan a target to be observed CO (ground surface area or sheet of water), containing at least one reversibly photoswitchable fluorescent species P (Dronpa, for example). The fluorescence emission FLU is collected by an objective of a camera CAM', which acquires an image of the target. As in the preceding case, a processor PR drives the modulator MEO and the camera CAM' so as to perform a detection in quadrature as described above.

Figure 13:
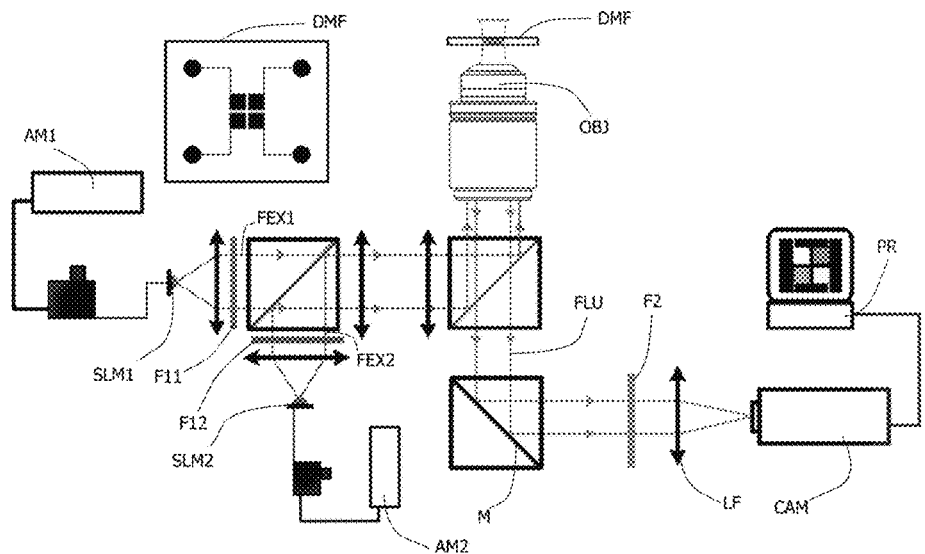
FIG. 13 schematically illustrates the experimental apparatus used to obtain FIG. 10.

FIG. 13 illustrates an apparatus for implementing a method according to an embodiment of the invention, of the type used to carry out some of the experimental validations described above. Such an apparatus, illustrated by way of nonlimiting example, comprises two light sources SLM1 and SLM2 consisting of two strips of light-emitting diodes. The light source SLM1 is powered by a power source AM1 and the light source SLM2 is powered by a power source AM2. The modulation of the excitation light beam FEX1 generated by said source is obtained by modulation of the electrical power supply. Since the emission of the light-emitting diodes is wideband, the beams FEX1 and FEX2 are filtered by two optical filters F11 and F12, before being directed onto a sample, consisting in this case of a microfluidic device DMF. The duly illuminated sample is observed, by its rear face, by an objective OBJ which collects the fluorescence emission and focuses it into a beam FLU. The latter is filtered (filter F2) and directed, via a mirror M and a lens LF, to a camera CAM. A processor PR (in fact, a computer appropriately programmed) drives the power sources AM1, AM2 and the camera CAM so as to perform a detection in quadrature as described above. To perform a simple detection or a titration, without imaging, the camera CAM can be replaced by a spot light sensor.

Figure 14:
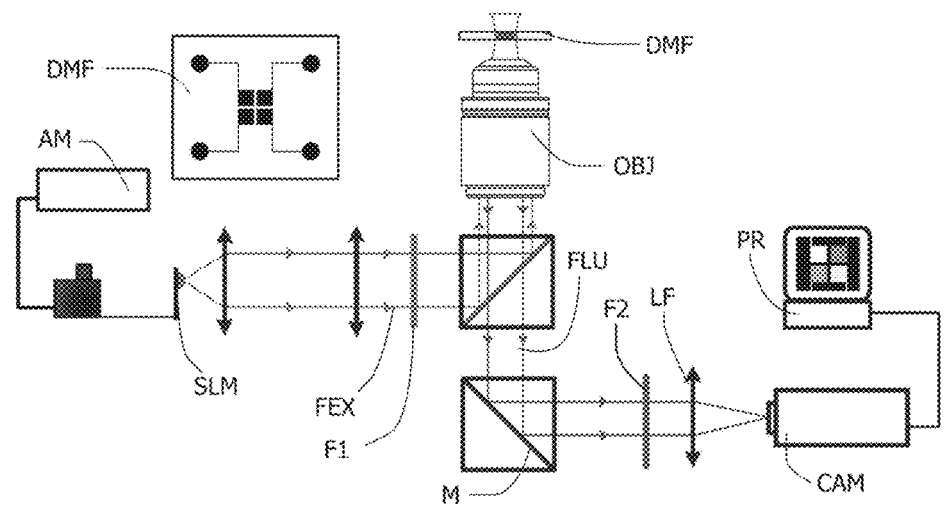
FIG. 14 schematically illustrates the experimental apparatus used to obtain FIG. 8.

FIG. 14 illustrates an apparatus for implementing a method according to an embodiment of the invention, of the type used to perform some of the experimental validations described above. Such an apparatus, illustrated by way of nonlimiting example, comprises a light source SLM consisting of a strip of light-emitting diodes, powered by a power source AM. The modulation of the excitation light beam FEX generated by said source is obtained by modulation of the electrical power supply. Since the emission of the light-emitting diodes is wideband, the beam FEX is filtered by a first optical filter F1, before being directed onto a sample, consisting in this case of a microfluidic device DMF. The duly illuminated sample is observed by an objective OBJ which collects the fluorescence emission and focuses it into a beam FLU. The latter is filtered (filter F2) and directed, via a mirror M and a lens LF, to a camera CAM. A processor PR (in fact, a computer appropriately programmed) drives the power source AM and the camera CAM so as to perform a detection in quadrature as described above. To perform a simple detection or a titration, without imaging, the camera CAM can be replaced by a spot light source.

The invention has been described by considering the case of a reversibly photoswitchable species emitting a fluorescence emission. However, the method for detection in quadrature which has just been described can also exploit any other spectroscopic observable making it possible to distinguish the two states of a reversibly photoswitchable species. By way of nonlimiting example, absorbance can be considered (in particular, in the low absorption regime, where the Beer-Lambert law can be linearized); in this case, instead of detecting a fluorescence emission, transmitted light intensity is detected which is related to an incident light intensity, then the amplitude of its component in phase quadrature is determined. Another example is reflectance. The equations 19-21 and 58-59, which define the optimal illumination conditions, apply whatever the spectroscopic observable considered.

The invention claimed is:

1. A method for detecting at least one reversibly photoswitchable fluorescent species, comprising the following steps:
   a) illuminating a sample containing said or at least one said reversibly photoswitchable fluorescent species with a periodically modulated illuminating light source; and b) detecting fluorescence emission, emitted by said duly illuminated sample and collected by an objective, with a light sensor;

further comprising the following steps:

c) extracting an amplitude of a component of an intensity of said fluorescence emission, detected by the light sensor, exhibiting a same periodicity as said periodically modulated illuminating light and in phase quadrature in relation thereto;

d) determining at least one element chosen from a presence and a concentration of one said reversibly photoswitchable fluorescent species from the component of the intensity of said fluorescence emission extracted in said step c);

and wherein an average intensity of said illuminating light and its modulation frequency for the periodically modulated illuminating light source are chosen so as to maximize said amplitude of the intensity component of said fluorescence emission.

2. The method of claim 1, wherein at least one said reversibly photoswitchable fluorescent species exhibits a first chemical state and a second chemical state, at least one of said states being fluorescent, said or each said reversibly photoswitchable fluorescent species being able to be switched from said first state to said second state by a first photo-induced reaction, then return to said first state both by a thermo-induced reaction and by a second photo-induced reaction, and in which said periodically modulated illuminating light exhibits an average intensity $I^0$ and is modulated at a frequency f with:

$$I^0 = \frac{k_{21}^\Delta}{\sigma_{12} + \sigma_{21}}$$

$$f = k_{21}^\Delta / \pi$$

wherein:
 $\sigma_{12}I^0$ and $\sigma_{21}I^0$ are, respectively, the kinetic constants of said first photo-induced reaction of said fluorescent species and of said second photo-induced reaction of said fluorescent species; and
 $k_{21}^\Delta$ is the kinetic constant of said thermo-induced reaction of said fluorescent species.

3. The method of claim 1, wherein, in said step a), said sample is illuminated by a substantially monochromatic illuminating light.

4. The method as of claim 1, wherein said illuminating light comprises a first substantially monochromatic illuminating light of wavelength $\lambda_1$ and a second substantially monochromatic illuminating light, of wavelength $\lambda_2$, different from $\lambda_1$, the first and the second said illuminating lights being adapted to induce the photoswitching of said states of at least one said reversibly photoswitchable fluorescent species and of which at least the first said illuminating light is periodically modulated.

5. The method of claim 4, wherein at least one said reversibly photoswitchable fluorescent species exhibits a first chemical state and a second chemical state, at least one of said states being fluorescent, said or each said reversibly photoswitchable fluorescent species being able to be switched from said first state to said second state by a first photo-induced reaction, then return to said first state by a second photo-induced reaction, and wherein said first illuminating light exhibits an average intensity $I_1^0$ and is modulated at a frequency f' and said second illuminating light exhibits a substantially constant intensity $I_2^0$ with:

$$\frac{I_2^0}{I_1^0} = \frac{\sigma_{12,1} + \sigma_{21,1}}{\sigma_{12,2} + \sigma_{21,2}}$$

$$\frac{f'}{I_1^0} = (\sigma_{12,1} + \sigma_{21,1})/\pi$$

wherein:
 $\sigma_{12,1}I_1^0$ and $\sigma_{21,1}I_1^0$ are, respectively, the kinetic constants of said first and said second reactions photoinduced by said first illuminating light; and
 $\sigma_{12,2}I_2^0$ and $\sigma_{21,2}I_2^0$ are, respectively, the kinetic constants of said first and said second reactions photoinduced by said second illuminating light.

6. The method of claim 1, wherein said sample contains a plurality of said reversibly photoswitchable fluorescent species exhibiting different dynamic properties, said steps a) to c) being implemented successively for the detection of at least two said reversibly photoswitchable fluorescent species.

7. The method of claim 1, wherein said steps b) and c) are implemented by lock-in detection of said fluorescence emission with a lock-in amplifier.

8. The method of claim 1, wherein said sample contains at least one other fluorescent species.

9. The method of claim 1, wherein said step d) also comprises the following step:
 d') determining by titration the concentration of said or of at least one said reversibly photoswitchable fluorescent species from the component of the intensity of said fluorescence emission extracted in said step c).

10. The method of claim 1, wherein said or at least one said reversibly photoswitchable fluorescent species is chosen from:
 a photochromic fluorescent protein; and
 a complex of a biomolecule with a fluorogenic probe.

11. The method of claim 1, wherein the sample can comprise biological material.

12. A fluorescence microscopy method implementing a method for detecting at least one reversibly photoswitchable fluorescent species, comprising the following steps:
 a) illuminating a sample containing said or at least one said reversibly photoswitchable fluorescent species with a periodically modulated illuminating light source; and
 b) detecting fluorescence emission, emitted by said duly illuminated sample and collected by an objective, with a light sensor;

further comprising the following steps:
 c) extracting an amplitude of a component of an intensity of said fluorescence emission, detected by the light sensor, exhibiting a same periodicity as said periodically modulated illuminating light and in phase quadrature in relation thereto;
 d) determining at least one element chosen from a presence and a concentration of one said reversibly photoswitchable fluorescent species from the component of the intensity of said fluorescence emission extracted in said step c);

and wherein an average intensity of said illuminating light and its modulation frequency for the periodically modulated illuminating light source are chosen so as to maximize said amplitude of the intensity component of said fluorescence emission.

13. An optical remote sensing method implementing a method for detecting at least one reversibly photoswitchable fluorescent species, comprising the following steps:
   a) illuminating a sample containing said or at least one said reversibly photoswitchable fluorescent species with a periodically modulated illuminating light source; and
   b) detecting fluorescence emission, emitted by said duly illuminated sample and collected by an objective, with a light sensor;
   further comprising the following steps:
   c) extracting an amplitude of a component of an intensity of said fluorescence emission, detected by the light sensor, exhibiting a same periodicity as said periodically modulated illuminating light and in phase quadrature in relation thereto;
   d) determining at least one element chosen from a presence and a concentration of one said reversibly photoswitchable fluorescent species from the component of the intensity of said fluorescence emission extracted in said step c);
   and wherein an average intensity of said illuminating light and its modulation frequency for the periodically modulated illuminating light source are chosen so as to maximize said amplitude of the intensity component of said fluorescence emission.

14. The method of claim 1, wherein said sample can comprise a living organism, and wherein at least one element chosen from the presence and the concentration of one said reversibly photoswitchable fluorescent species is measured from the component of the intensity of said fluorescence emission extracted in said step c) without performing any sampling on said living organism.

15. The method of claim 13, wherein said illuminating light is emitted in a direction and wherein said periodic modulation of said illuminating light is implemented by a modulation of said direction of emission of said illuminating light.

16. The method of claim 2 wherein said illuminating light comprises a part of the daylight and wherein said part of the daylight participates in the light intensity received by said reversibly photoswitchable fluorescent species by remaining less than or equal to said intensity $I^0$.

17. The method of claim 1, further comprising:
   implementing a processor and a power source for the periodically modulated illuminating light source;
   driving the power source for the periodically modulated illuminating light source with the processor; and
   driving the light sensor with the processor.

* * * * *